United States Patent [19]

Sorenson

[11] Patent Number: 5,541,174
[45] Date of Patent: Jul. 30, 1996

[54] ANALGESIC METHOD

[76] Inventor: John R. J. Sorenson, 4301 W. Markham, Little Rock, Ark. 72201

[21] Appl. No.: 375,184

[22] Filed: Jan. 18, 1995

Related U.S. Application Data

[63] Continuation of Ser. No. 8,538, Jan. 25, 1993, abandoned, which is a continuation of Ser. No. 663,727, Mar. 4, 1991, Pat. No. 5,216,021, which is a division of Ser. No. 426,456, Oct. 20, 1989, Pat. No. 4,999,347, which is a division of Ser. No. 901,191, Aug. 28, 1986, abandoned.

[51] Int. Cl.$^6$ .................... A61K 31/30; A61K 31/555
[52] U.S. Cl. .................................. 514/186; 514/499
[58] Field of Search ...................... 514/499, 419, 514/186

[56] References Cited

U.S. PATENT DOCUMENTS

| | | | |
|---|---|---|---|
| 4,440,754 | 4/1984 | Sorenson | 514/499 |
| 4,680,309 | 7/1987 | Mauer | 514/499 |

*Primary Examiner*—Raymond Henley, III
*Attorney, Agent, or Firm*—Wood, Herron & Evans

[57] ABSTRACT

Disclosed herein are analgesic copper coordination compounds and a process for using them in the treatment of analgesia in animal bodies. The copper coordination compounds utilized are the reaction products of copper salts with:

1. carboxylic acids or their alkaline earth salts;

2. aromatic carboxylic acids or their alkaline earth salts;

3. heterocyclic carboxylic acids or their alkaline earth salts;

4. amino acids or their alkaline earth salts;

5. anthranilic acids or their alkaline earth salts;

6. salicylic acids or their alkaline earth salts;

7. acetylsalicylates or their alkaline earth salts;

8. arylacetic acids or their alkaline earth salts;

9. disubstituted aminodithiocarbamates, and mixtures of any of the above.

The process disclosed comprises administering to animals, orally or parenterally, in controlled dosages, the aforementioned copper coordination compounds.

7 Claims, 1 Drawing Sheet

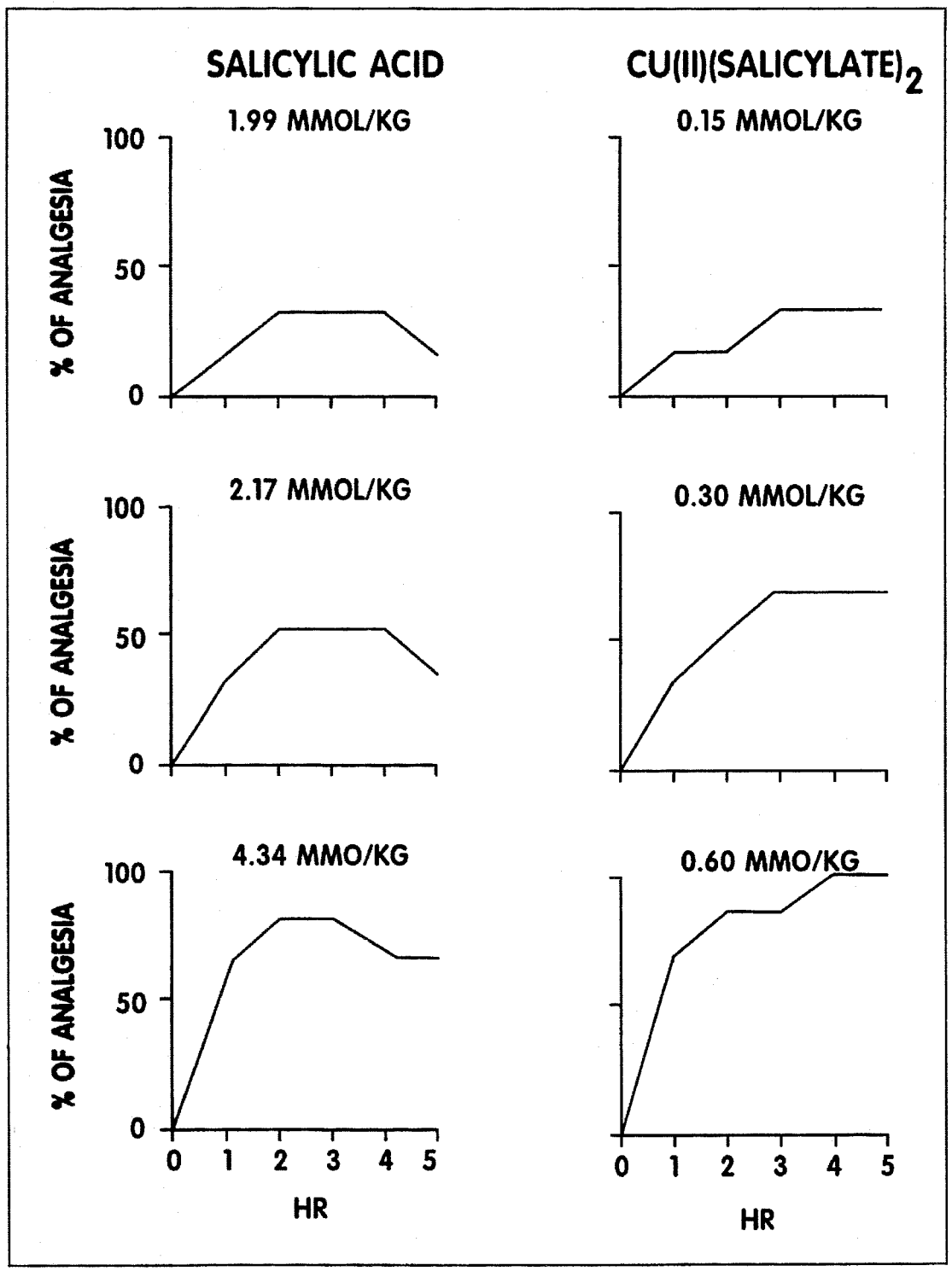

ANALGESIC METHOD

This application is a continuation of application Ser. No. 08/008,538, filed on Jan. 25, 1993, now abandoned, which is a continuation of U.S. application Ser. No. 07/663,727, filed Mar. 4, 1991, now U.S. Pat. No. 5,216,021, which is a division of U.S. application Ser. No. 07/426,456, filed Oct. 20, 1989, now U.S. Pat. No. 4,999,347, which in turn is a division of U.S. application Ser. No. 06,901,191, filed Aug. 28, 1986, now abandoned.

BACKGROUND OF THE INVENTION

Morphine, while a strong, analgesic, is of course very addictive and consequently its use must be strictly controlled and monitored. While there are various antiinflammatory compounds that are mild analgesics that are not addictive, their use is limited because of their low order of weak activity. Some, too, are antiinflammatory but their use is limited because they are ulcergenic.

It has therefore been a principal objective of my invention to provide an analgesic treatment utilizing more potent compounds. It has also been an objective to provide such a treatment with compounds whose analgesic activity approach and equal or exceed that of morphine.

SUMMARY OF THE INVENTION

It has been quite unexpectedly discovered that copper coordination compounds produced by reacting alkaline earth salts of the following classes of organic compounds with loosely bonded forms of copper to produce products which when used in accordance with the following processes, exhibit excellent analgesic activity in animals, i.e., a warm-blooded animal or mammalian subject:

1. carboxylic acids or their alkaline earth salts;
2. aromatic carboxylic acids or their alkaline earth salts;
3. heterocyclic carboxylic acids or their alkaline earth salts;
4. amino acids or their alkaline earth salts;
5. anthranilic acids or their alkaline earth salts;
6. salicylic acids or their alkaline earth salts;
7. acetylsalicylates or their alkaline earth salts;
8. arylacetic acids or their alkaline earth salts;
9. disubstituted aminodithiocarbamates, and mixtures of any of the above.

More particularly, the following classes of organic compounds and the specified copper coordination compounds produced therefrom have proven to be especially useful:

a. Salicylic Acids: $Cu(II)(salicylate)_2$, $CU(II)(3,5-diisopropylsalicylate)_2$ b. Acetylsalicylic Acids (an aromatic carboxylic acid): $Cu(II)_2(Acetylsalicylate)_4$ c. Anthranilic Acids: $Cu(II)(anthranilate)_2$ d. Nicotinic Acids: $Cu(II)_2$ {2-[3-(trifluoromethyl)phenyl]aminonicotinate}$_4$ e. Arylacetic Acids: $Cu(II)_2[1$-chlorobenzoyl)-5-methoxy-2methyl-3-indolylacetate]$_4$ f. Amino Acids: $Cu(II)(alaninate)_2$, $Cu(II)(cystinate)_2$, and $Cu(II)(glycinate)_2$ g. Carboxylic Acids: $Cu(II)_2(acetate)_4$ h. Disubstitutedaminodithiocarbamates: $Cu(II)(diethyldithiocarbamate)_2$ It has been empirically determined that the copper coordination compounds disclosed herein not only demonstrate excellent anti-inflammatory activity and anti-ulcer activity but they are also excellent analgesics. Some of the compounds of the present invention have an activity that approaches that of morphine.

The compounds can be administered orally or parenterally. The copper coordination compounds, being relatively insoluble in water, are administered by suspending them in saline solution to which a suitable suspending agent has been added.

In treating pain by injecting test animals with the cooper coordination compound so prepared it has been found that excellent results, in the test models hereinafter described, may be obtained if the dosages administered comprise about 0.1–500 mg. per kilogram of body weight.

In using the compounds of the present invention it has been found that excellent results are obtained if the dosages administered comprise about 0.5 to 400 mg. per kilogram of body weight.

DESCRIPTION OF THE DRAWING

The drawing illustrates the time course of analgesia of $Cu(11)(salicylate)_2$ versus salicylic acid in the adjuvant-induced arthritic pain model.

DETAILED DESCRIPTION OF THE INVENTION

For the purpose of more fully understanding the present invention, a copper coordination compound is intended to mean a compound whose molecular structure contains one or more copper atoms bonded to one or more atoms of one or more molecules or ions by coordinate covalent bonds.

The copper coordination compounds of the present invention are prepared by reacting copper salts, preferably cupric chloride or cupric acetate with a member of the following classes of organic compounds:

1. carboxylic acids or their alkaline earth salts;
2. aromatic carboxylic acids or their alkaline earth salts;
3. heterocyclic carboxylic acids or their alkaline earth salts;
4. amino acids or their alkaline earth salts;
5. anthranilic acids or their alkaline earth salts;
6. salicylic acids or their alkaline earth salts;
7. acetylsalicylates or their alkaline earth salts;
8. arylacetic acids or their alkaline earth salts;
9. disubstituted aminodithiocarbamates, and mixtures of any of the above.

More specifically, it has been found that suitable compounds may be produced by reacting cupric chloride with the sodium salts of L & D tryptophan, anthranilic acid, 3,5-diisopropylsalicylic acid, acetylsalicylic acid, hydrocortisone-21-phosphate, dexamethasone-21-phosphate, salicylic acid, 3-p-chlorophenyl-3, 4, 5, 6, -tetrahydro-β-carboline-5-carboxylic acid, 3, 4, 5, 6-tetra-hydro-β-carboline-5-carboxylic acid, and 1-(p-chlorobenzoyl)-5-methoxy-2-methylinodole-3-acetic acid; by reacting cupric chloride with 1-phenyl-5-aminotetrazole, ∈-aminocaproic acid, pyridine, a mixture of D and L-tryptophan, morpholine, and histamine; by reacting cupric chloride with the ammonium salt of hydrocortisone-21-hemisuccinic acid; by reacting cupric acetate with the sodium salts of 2[3(trifluoro-methyl)phenyl] aminonicotinic acid (sometimes referred to hereinafter as niflumic acid), 1-carboxyisoquinoline, phenylcinchoninic acid, hydrocortisone-21-phosphate, and 4-n-butyl-1,2-diphenyl-3,5-pyrazolidinedione; by reacting cupric acetate with the ammonium salt of nicotinic acid; by reacting cupric acetate with D-pencillamine, 1-phenyl-5-aminotetrazole, D or L-aspartic acid, L-lysine, 2-carboxyindole; and by reacting cupric acetate with the potassium salt of 17-hydroxy-3-oxo-17 α-pregn-4,6-diene-21 carboxylic acid.

It is preferable to produce copper coordination solvates rather than anhydrous compounds as will be more fully appreciated by the following description. The compounds may be solvated with a lower alcohol (methanol or ethanol), acetone, pyridine, water or dimethyl sulfoxide.

Following is a more detailed description of how the copper coordination compounds of the present invention may be prepared. Not all have been empirically determined.

EXAMPLE 1

Bis-L-tryptophanato(O,N)copper(II), [Cu(II)(L-tryptophan)$_2$].

L-tryptophan (5.0 g, 0.025 mol) was dissolved in 100 ml of H$_2$O with a solution of NaOH (50%), filtered and back titrated if necessary with a solution of HCl (10%) until indicator paper showed the solution to be weakly basic. This solution was then dropped into 100 ml of H$_2$O containing CuCl$_2$ dihydrate (3.3 g, 0.021 mol). After stirring for about one hour a precipitate formed and was collected by filtration. This blue precipitate was washed with H$_2$O and diethylether, dried at 100° and 15 mm Hg overnight and weighed (4.7 g, 82% yield). A sample of this material on heating turned brown at 240° C. and finally decomposed at 260° C.

Analysis Calcd. for C$_{22}$H$_{22}$N$_4$O$_4$Cu: C, 56.22; H, 4.72; N, 11.92. Found: C, 56.07; H, 4.89 and N, 12.16.

EXAMPLE 2

Bis-D-tryptophanato(O,N)copper(II)[Cu(II)(D-tryptophan)$_2$].

This coordination compound was prepared as described for the L isomer (example 1) using 5.0 g, 0.021 mol of D-tryptophan. After collecting the precipitate by filtration, washing with H$_2$O, diethylether and acetone (250 ml), the precipitate was dried overnight at 100° and 15 mm Hg and weighed (4.3 g, 75% yield). A sample of this material decomposed slowly on heating to 269° C.

Analysis Calcd. for C$_{22}$H$_{22}$N$_4$O$_4$Cu: C, 56.22; H, 4.72; N, 11.92. Found: C, 56.10, H, 4.72 and N, 12.00.

EXAMPLE 3

Bisanthranilato(O,N)copper(II), [Cu(II)(anthranilate)$_2$].

The sodium salt of anthranilic acid (5 g 0.04 mol) was prepared as described in example 1 in 150 ml of H$_2$O with 50% NaOH. This solution was dropped into 300 ml of a stirred aqueous solution of CuCl$_2$ dihydrate (2.5 g, 0.016 mol). The precipitate which formed was removed by filtration and washed with H$_2$O and diethylether (5×50 ml). After drying overnight @ 120° C. and 15 mm Hg the material weighed 6.1 g, 99% yield. A sample of this greenish-blue material decomposed on heating to 240° C. and continued to decompose on heating to 290° C.

Analysis Calcd. for C$_{14}$H$_6$N$_2$O$_4$Cu: C, 50.07; H, 3.60; N, 8.35. Found: C, 50.07; H, 3.77; N, 8.42.

EXAMPLE 4

Bis(3,5-diisopropylsalicylato(O,O)copper(II)]Cu(II)(3,5-dips)$_2$].

A solution of the sodium salt of 3,5-diisopropylsalicylic acid (5 g, 0.023 mol) was prepared as described in example 1 and added to 300 ml of a stirred aqueous solution of CuCl$_2$ dihydrate (1.59 g, 0.0336 mol). A brown precipitate formed which when recrystallized from ether gave green crystals. These crystals were filtered and dried at 125° C. and 15 mm Hg for three hours. The resulting brown crystalline material melted with decomposition over the range of 142°–144° C.

Analysis Calcd. for C$_{26}$H$_{34}$O$_3$Cu: C, 61.70; H, 6.77. Found: C, 61.49; H, 6.83.

EXAMPLE 5

Tetra(η-acetylsalicylato)biscopper(II), [Cu(II)$_2$(aspirinate)$_4$].

The sodium salt of acetylsalicylic acid was prepared by dissolving acetylsalicylic acid (30 g, 0.165 mol) in 200 ml of H$_2$O at 0° C. with 50% NaOH so that the pH did not go above 11.0 and rarely reached 11.0. This was done over a period of 45 to 60 minutes. The final pH of the solution was about 8.7. The CuCl$_2$ solution prepared by adding 56.5 g, 0.330 mol of CuCl$_2$ dihydrate to 500 ml of water, was added to a stirred solution of sodium acetylsalicylate during a period of 10 to 15 minutes. Following the completion of this addition the blue precipitate was collected by filtration; washed with H$_2$O (500 ml×2), acetone (400 ml×2) and diethylether (300 ml) and left to dry on a filter funnel attached to a water aspirator. After two days the powder was dried at 50° C. for 6–7 hours and weighed (31.3 g, 90.6% yield).

Analysis calculated for C$_{36}$H$_{28}$O$_{16}$Cu$_2$: C, 51.25; H, 3.35; Found: C, 51.20; H, 3.51.

EXAMPLE 6

[2[3(trifluoromethyl)phenyl]aminonicotinato]$_{2n}$-(aqua)$_n$-copper(II)$_n$, [Cu(II)$_n$(niflumate)$_{2n}$(H$_2$O)$_n$].

The sodium salt of 2[3(trifluoromethyl)phenyl]] aminonicotinic acid (20 g, 0.0708 mol) was prepared as described in example 1. The solution of this salt was then added to about 300 ml of a saturated, stirred solution of cupric acetate monohydrate. The resultant greenish precipitate was collected by filtration and dissolved in 200 ml of diethylether. The ether solution was then dropped into about 4 liters of boiling skellysolve A. The resultant precipitate was collected from the hot solution by filtration, dried at 125° C. for three hours at 15 mm Hg and weighed (16 g, 70% yield). A sample of this material melted with decomposition over the range of 201° to 208° C.

Analysis Calcd. for C$_{52}$H$_{36}$O$_{10}$N$_8$F$_{12}$Cu: C, 48.49; H, 2.82; N, 8.70. Found: C, 48.53, H, 2.66; N, 8.91.

EXAMPLE 7

D-penicillaminato-(aqua)$_{1.5}$-copper(I), [Cu(I)$_n$(D-pen)$_n$(H$_2$O)$_{1.5n}$].

D-penicillamine (5 g, 0.0335 mol) was dissolved in 50 ml of water. The solid cupric acetate monohydrate (6.68 g, 0.017 mol) was then added to the solution at such a rate so as to not exceed its rate of solution. Upon the completion of this addition the solution was dark gray. About 50–100 ml of H$_2$O was then added and the mixture left to stir for about 30 minutes. The resultant gray precipitate was collected by filtration leaving a blue filtrate (125 ml). This blue filtrate was subsequently diluted with about 375 ml of acetone and set aside for use in example 8. The air-dried gray powder weighed 4.3 g, 54.0% yield. A sample of this material decomposed over the range of 155°–157° C.

Analysis Calcd. for $C_5H_9SNO_{3.5}Cu$: C, 25.26; H, 5.10, N, 5.89. Found: C, 25.32; H, 5.03; N, 5.47.

EXAMPLE 8

(D-penicillaminato)$_{2n}$-(aqua)$_{2n}$-copper(II), [Cu(II)$_n$(D-pen)$_{2n}$(H$_2$O)$_{2n}$].

On standing, the acetone diluted blue filtrate described in the preparation of Example 7 gave a gray precipitate which was collected by filtration and this filtrate also set aside. The gray solid was washed with 60 ml of water and the remaining light tan solid washed with 60 ml of acetone air dried and weighed (1.15 g, 17.4% yield). A sample of this solid melted with decomposition over the range of 155° to 157° C.

Analysis Calcd. for $C_{10}H_{24}O_6S_2N_2Cu$: C, 30.33; H, 6.11; N, 7.08. Found: C, 30.42; H, 6.49; N, 6.72.

EXAMPLE 9

(D-pencillamine disulfide)$_n$-(aqua)$_{3n}$copper(II)$_n$,[Cu(II)$_n$(D-pen disulfide)$_n$(H$_2$O)$_{3n}$].

The acetone-water filtrate obtained after removing example 8 from the blue acetone filtrate, described above, was concentrated to about 100 ml and diluted with 400 ml of acetone. A blue precipitate (1.3 g, 9.4% yield) was obtained following filtration, washing with acetone and air drying. A sample of this material decomposed over the range of 157° to 158° C. After drying twice at 73° and 15 mm Hg overnight a sample of this material decomposed over the range of 172° to 175° C.

Analysis Calcd. for $C_{10}H_{24}N_2S_2O_7Cu$: C, 29.15; H, 5.87; N, 6.80. Found: C, 29.43; H, 5.76; N, 6.36.

EXAMPLE 10

(Acetato)$_{2n}$-(1-phenyl-5-aminotetrazolato)$_n$-copper(II)$_n$, [Cu(II)$_n$(pat)$_n$(acetate)$_{2n}$].

Five grams of cupric acetate monohydrate (0.012 mol) was dissolved in 20 ml of H$_2$O. This solution was diluted with 100 ml of methanol. 5 g (0.31 mol) of 1-phenyl-5-aminotetrazole was added to obtain a blue gel. This gel was filtered and the resulting blue flakes were washed with about 400 ml of methanol until the washings were no longer blue. The filtrate was then concentrated to about 150 ml and stored for about one week in the refrigerator. A precipitate formed and was removed by filtration. This green crystalline solid was air dried and weighed (3.8 g, 17.9% yield). A sample of this solid decomposed over the range of 186°–189° C.

Analysis Calcd. for $C_{22}H_{26}N_{10}O_8Cu_2$: C, 38.54; H, 3.82; N, 20.43. Found: 38.42; H, 3.94; N, 20.92.

EXAMPLE 11

(1-phenyl-5-aminotetrazolato)$_{2n}$-(chloride)$_{2n}$-copper(II)$_n$, [Cu(II)$_n$(pat)$_{2n}$ (HCl)$_{2n}$].

Five grams (0.012 mol) of 1-phenyl-5-aminotetrazole was dissolved in 30 ml of methanol, then 5 g (0.029 mol) of CuCl$_2$ dihydrate dissolved in 25 ml of methanol was added to the stirred solution of tetrazole. The resulting solution was filtered and set aside. Three subsequent crops of a green solid were obtained following filtration and concentration of the filtrate. The combination of these were air dried and weighed (5 g, 17.7% yield). A sample of this material decomposed on heating over the range of 184° to 185° C.

Analysis Calcd. for $C_{14}H_{14}N_{10}CuCl_2$: C, 36.81; H, 3.09; N, 30.67. Found: C, 36.65; H, 3.17; N, 31.03.

EXAMPLE 12

(D-Asparato)$_n$(aqua)$_{3.5n}$-copper(II)$_n$, [Cu(II)$_n$(D-aspartate)$_n$(H$_2$O)$_{3.5n}$].

This material is made in a manner similar to the preparation of example 1 using D-aspartic acid in place of L-tryptophan.

Analysis calculated for $C_4H_{12}N\ O_{7.5}Cu$: C, 18.69; H, 4.66. Found: C, 18.55; H, 4.92.

EXAMPLE 13

(L-Aspartato)$_n$-(aqua)$_{3.5n}$-copper(II)$_n$, [Cu(II)$_n$(L-aspartate)$_n$(H$_2$O)$_{3.5n}$].

This material is made in a manner similar to the preparation of example 1 using L-aspartic acid in place of L-tryptophan.

Analysis calculated for $C_4H_{12}N\ O_{7.5}Cu$: C, 18.69; H, 4.66. Found: C, 18.41; H, 4.73.

EXAMPLE 14

(L-Lysino)$_n$-(chloro)$_{2n}$-(aqua)$_n$-copper(II)$_n$, [Cu(II)$_n$, (L-lysinate)$_n$(Cl)$_{2n}$(H$_2$O)$_n$].

This material is made in a manner similar to example 1 using L-lysine in place of L-tryptophan. A sample of this material decomposed on heating over the range of 169° to 170° C.

Analysis calculated for $C_6H_{16}N_2O_3CuCl_2$: C, 24.10; H, 5.40; Cl, 23.70; N, 9.38. Found: C, 24.54; H, 5.07; Cl, 24.00; N, 9.36.

EXAMPLE 15

(L-Lysino)$_{2n}$-(chloro)$_{2n}$-(aqua)$_n$-copper(II)$_n$, [Cu(II)$_n$(L-lysinate)$_{2n}$(Cl)$_{2n}$(H$_2$O)$_n$].

This material is made in a manner similar to example 1 using L-lysine in place of L-tryptophan. A sample of this compound decomposed on heating up to and over the range 210° to 214° C.

Analysis calculated for $C_{12}H_{32}N_4O_5CuCl_2$: C, 32.40; H, 6.80; Cl, 12.60. Found: C, 32.56; H, 7.04; Cl, 12.24.

EXAMPLE 16

Bis(D,L-tryptophanato(O,N)copper(II), [Cu(II)(D,L-tryptophan)$_2$].

This coordination compound was prepared and isolated as described in example 1 using a mixture of D and L-tryptophan in place of L-tryptophan.

Analysis Calcd. for $C_{22}H_{22}N_4O_4Cu$: C, 56.22; H, 4.72. Found: C, 55.58; H, 4.87.

EXAMPLE 17

(ε-aminocaproato)$_n$-(chloro)$_{1.5n}$-(methanol)$_{0.5n}$-copper(II)$_n$, [Cu(II)$_n$(ε-aminocaproate)$_n$(Cl)$_{1.5n}$(CH$_3$OH)$_{0.5n}$]. This coordination compound was prepared by stirring a suspension of 10 g (0.08 mol) of ε-aminocaproic acid in 200 ml of methanol and slowly adding 10 g (0.065 mol) of solid cupric chloride dihydrate. The resultant green precipitate was collected by filtration washed with methanol, dried at 25° C. and 15 mm Hg overnight, and weighed (10.5 g, 51% yield). A sample of this material decomposed over the range of 157° to 158° C.

Analysis Calcd. for $C_7H_{15.5}O_{2.5}CuCl_{1.5}$: C, 29.53; H, 5.91; Cl, 20.11. Found: C, 29.97; H, 6.06; Cl, 20.36.

EXAMPLE 18

($\epsilon$-aminocaproato)$_n$-(chloro)$_{2n}$-(aqua)$_{0.5n}$-copper(II)$_n$, [Cu(II)$_n$($\epsilon$-aminocaproate)$_n$(Cl)$_{2n}$(H$_2$O)$_{0.5n}$].

This coordination compound was obtained from the filtrate described in example 17. Following concentration of the filtrate and methanol washings to about 100 ml of bluish-green precipitate formed. This precipitate was collected by filtration dried at 25° C. at 15 mm Hg and weighed (4.6 g, 21% yield). A sample of this material decomposed on heating over the range of 193° to 194° C.

Analysis Calcd. for $C_6H_{14}NO_{2.5}Cl_2Cu$: C, 26.24; H, 5.14; Cl, 25.82. Found: C, 26.29; H, 5.28; Cl, 25.39.

EXAMPLE 19

Tetra($\eta$acetato)bis(monopyridino)copper(II), [Cu(II)$_n$(pyridine)$_n$(acetate)$_{2n}$].

This coordination compound was prepared by adding 10 g (0.025 mol) of cupric acetate monohydrate to 70 ml of pyridine and the mixture heated while stirring at 100° C. The hot suspension was filtered and the resulting precipitate collected by filtration and washed with 200 to 300 ml of diethylether. A sample of this green solid decomposed on heating over the range of 214° to 216° C. When the ether-pyridine filtrate cooled a second precipitate, which was bluish, was obtained. Removal by filtration and washing with ether gave a second crop of the green material in the filtrate. This green solid had a decomposition range of 216° to 218° C. A mixture decomposition range of 216° to 218° C. was observed for a sample of the combination of the two green solids. Total yield was 12 g, 92%.

Analysis Calcd. for $C_{18}H_{22}N_2O_8Cu_2$: C, 41.46, H, 4.25; N, 5.37. Found: C, 41.87; H, 4.54; N, 5.23.

EXAMPLE 20

Bispyridinobischlorocopper(II), [Cu(II)(pyridine)$_2$(Cl)$_2$].

This composition was prepared by dissolving 9.42 g (0.062 mol) of CuCl$_2$ dihydrate in 95% ethanol and adding 15 g (0.19 mol) of pyridine slowly to the stirred solution. The resultant blue precipitate was removed by filtration, washed with 95% ethanol (200 ml), dried at about 50° C. for 24 hours and weighed (19.8 g, 35.6% yield). A sample of this material decomposed over the range of 225° to 275° C.

Analysis Calcd. for $C_{10}H_{10}N_2CuCl_2$: C, 41.32; H, 3.44. Found: C, 41.25; H, 3.52.

EXAMPLE 21

Bismorpholoniumtetrachlorocopper(II), [Cu(II)(morpholine)$_2$(Cl)$_2$(HCL)$_2$].

This coordination compound was prepared according to the published procedure of W. H. C. Rueggeberg, G. N. Jarman and R. B. Wearn, J.A.C.S., 69, 1222 (1947) incorporated by reference herein. Starting with 14.5 g (0.167 mol) of morpholine the coordination compound was obtained in 41% yield. A sample of this green crysalline melted with decomposition over the range of 167°–170° C.

Analysis Calcd. for $C_8H_{20}N_2O_2CuCl_4$: C, 25.17; H, 5.28; N, 7.34. Found: C, 25.17; H, 5.41; N, 7.21.

EXAMPLE 22

(Histamino)$_n$-(chloro)$_{2n}$-(hydrochloro)$_{2n}$-copper(II)$_n$, [Cu(II)$_n$(histamine)$_n$(Cl)$_{2n}$(HCl)$_{2n}$].

This coordination compound was prepared by mixing 5 g (0.048 mol) of cupric chloride dihydrate in 200 ml of metahnol and concentrating to 135 ml. On standing a tan solid precipitated. This was removed by filtration and the filtrate concentrated to 80 ml. Upon addition of 40 ml of diethylether to this concentrate a light green solid precipitated. After removal by filtration and air drying this material was weighed (4.0 g, 23% yield). A sample decomposed over the range of 185° to 189° C. with softening at 182° C.

Analysis Calcd. for $C_5H_{10}N_3Cl_4Cu$: C, 18.91; H, 3.17; N, 13.24. Found: C, 18.90, H, 3.30; N, 13.30.

EXAMPLE 23

(Sodium)$_4$-(salicylato)$_4$-copper(II)$_2$, [Cu(II)$_2$(salicylate)$_4$(Na)$_4$].

This material was prepared from the material obtained in example 24 with the addition of sodium ethoxide in suitable solvent.

Analysis calculated for $C_{28}H_{16}O_{12}Cu_2Na_4$ were found to be within ±0.4% of the theoretical values.

EXAMPLE 24

(Salicylato)$_{2n}$-(aqua)$_{4n}$-copper(II)$_n$, [Cu(II)(Salicylate)$_2$(H$_2$O)$_4$].

This material may be prepared as described in example 1 using salicylic acid in place of L-tryptophan.

Analysis calculated for $C_{14}H_{18}O_{10}Cu$: C, 41.03; H, 4.43. Found: C, 41.24; H, 4.52.

EXAMPLE 25

(Pyridine-3-carboxylato)$_{2n}$-(aqua)$_{1.5n}$-copper(II), [Cu(II)$_{2n}$(nicotinate)$_{4n}$ (H$_2$O)$_{3n}$].

This coordination compound was prepared by dissolving 10 g (0.08 mol) nicotinic acid in 100 ml of water with concentrated NH$_4$OH so that the final pH was 7.0. A cupric chloride solution, prepared by dissolving 21.6 g (0.14 mol) of cupric chloride dihydrate in 200 ml of water, was stirred while the ammonium salt of nicotinic acid was added dropwise. The blue precipitate was collected by filtration, washed with 500 ml of water and air dried. The resulting material was dried at 80° C. and weighed (10.7 g, 80% yield). A sample of this material decomposed on heating up to and through the range of 265° to 266° C.

Analysis Calcd. for $C_{24}H_{22}O_{11}N_4Cu_2$: C, 43.05; H, 3.31; N, 8.37. Found: C, 43.25; H, 3.00; N, 8.12.

EXAMPLE 26

(Isoquinoline-1-carboxylato)$_{2n}$-copper(II)$_n$, [Cu(II)$_n$(1-carboxyisoquinoline)$_{2n}$].

The copper coordination compound of 1-carboxyisoquinoline (5 g 0.029 mol) was prepared by adding to its solution of the sodium salt, prepared as in example 1 in 200 ml of water using 1-carboxyisoquinoline in place of L-tryptophan, 60 ml of a saturated aqueous solution of cupric acetate monohydrate. The resultant purple precipitate was collected by filtration, washed with 500 ml of water and dried overnight at 100° C. and 15 mm Hg. A sample of this material (4.0 g, 70.2% yield) decomposed over the range of 295° to 296° C.

Analysis Calcd. for $C_{20}H_{12}N_2O_4Cu$: C, 58.84; H, 2.97; N, 6.87. Found: C, 58.49; H, 3.14; N, 6.79.

EXAMPLE 27

(2-Phenyl-4-isoquinoline-carboxylato)$_{2n}$-(aqua)$_{2n}$-copper(II)$_n$, [Cu(II)$_n$(2-phenyl-4-carboxyisoquinoline)$_{2n}$(H$_2$O)$_{2n}$].

This coordination compound was synthesized from the sodium salt of phenylcinchoninic acid (25 g, 0.15 mol), which was prepared as described in example 1 using "2-phenyl-4-isoquinoline-carboxylic acid" in place of L-tryptophan in 550 ml of water. The solution of the sodium salt was dropped into a stirred solution of cupric chloride dihydrate (14.2 g, 0.09 mol). The resulting green precipitate was collected by filtration, washed with methanol, water and then air dried and weighed (29.5 g, 67% yield). A sample of this material decomposed on heating over the range of 228° to 229° C.

Analysis Calcd. for $C_{64}H_{48}N_4O_{12}Cu_2$: C, 64.48; H, 4.06; N, 4.70. Found: C, 64.55; H, 3.80; N, 4.61.

EXAMPLE 28

(Indole-2-carboxylato)$_{3n}$-(acetato)$_n$-(aqua)$_{0.5n}$, [Cu(II)$_n$(2-carboxyindole)$_{3n}$(acetate) $_n$(H$_2$O)$_{0.5n}$].

This copper coordination compound was prepared from the parent acid 2-carboxyindole (4.5 g, 0.028 mol) as in example 1, using cupric acetate. The green precipitate was collected by filtration, air dried for several days, suspended in boiling methanol and again collected by filtration. It was then dried at 100° C. and 15 mm Hg overnight and at 125° and 15 mm Hg for 3 hours. A sample of this material (3.0 g, 23.3% yield) decomposed over the range of 249°–255° C.

Analysis Calcd. for $C_{29}H_{22}N_3O_9Cu$: C, 56.91; H, 3.59; N, 6.86. Found: C, 56.87; H, 4.03; N, 6.62.

EXAMPLE 29

(Indole-2-carboxylato)$_{3n}$-(acetato)$_n$-(aqua)$_{3.5n}$, [Cu(II)$_n$(2-carboxyindole)$_{3n}$(acetate) $_n$(H$_2$O)$_{0.5n}$].

This material was prepared as described in example 1 using 2-carboxyindole in place of L-tryptophan and dried at 100° C. and 15 mm Hg over the weekend. A sample of this material did not melt but did turn brown, as did the material in example 28, on heating to 260°.

Analysis Calcd. for $C_{29}H_{28}N_3O_{12}Cu$: C, 52.29; H, 4.20; N, 6.30. Found: C, 51.85; H, 3.78; N, 6.59.

EXAMPLE 30

(3-p-chlorophenyl-3,4,5,6-tetrahydro-β-carboline-5-carboxylato)$_{2n}$-(aqua)$_{2n}$-copper(II)$_n$, [Cu(II)$_n$(cp-tcca)$_{2n}$(H$_2$O)$_{2n}$].

The copper coordination compound of the parent acid (5 g, 0.015 mol) was prepared as described for example 1 except 3-p-chlorophenyl-2,3,4,5,6-tetrahydro-β-carboline-5-carboxylic acid was substituted for L-tryptophan. An olive drab precipitate was collected by filtration, washed with 500 ml of H$_2$O, 300 ml of diethylether and then with acetone until the washings were colorless. This material was dried at 100° C. overnight and 110° C. at 15 mm Hg for 3 hours before dissolving in acetone and precipitated with Skellysolve B. This material (2 g, 40% yield) was then dried overnight at 60° C. and 15 mm Hg and again at 125° C. and 15 mm Hg. A sample of this material decomposed over the range of 205° to 210° C.

Analysis Calcd. for $C_{36}H_{32}Cl_2N_4O_6Cu$: C, 57.56; H, 4.30; N, 7.46. Found: C, 57.16; H, 4.15; N, 6.96.

EXAMPLE 31

(3,4,5,6-Tetrahydro-β-carboline-5-carboxylato)$_{2n}$(aqua)$_{2.5n}$-copper(II)$_n$, [Cu(II)$_n$(tcca)$_{2n}$(H$_2$O)$_{2.5n}$].

The copper coordination compound of the parent acid (5 g, 0.023 mol) was prepared as described for example 1 except that 3,4,5,6-tetrahydro-β-carboline-5-carboxylic acid was substituted for L-tryptophan. This dark green solid was washed with 500 ml of water, then suspended in 500 ml of boiling acetone and collected by filtration. Drying was done at 100° C. at atmospheric pressure for 24 hours and then at 110° C. and 15 mm Hg for 3 hours. Subsequent leaching with hot propylene glycol gave an insoluble material (3.3 g, 52.8% yield) which rapidly decomposed on heating to 294° C.

Analysis Calcd. for $C_{24}H_{27}N_4O_{6.5}Cu$: C, 53.47; H, 5.05 and N, 10.40. Found: C, 53.54; H, 4.69 and N, 10.58.

EXAMPLE 32

(Hydrocortisone-21-phosphato)$_{2n}$-(aqua)$_{9n}$-copper(II)$_{3n}$, [Cu(II)$_{3n}$(HC-21-phosphate)$_{2n}$(H$_2$O)$_{9n}$].

This coordination compound was prepared by dissolving 1 g (0.002 mol) of the disodium salt of hydrocortisone-21-phosphate in 25 ml of water and adding this solution dropwise to a stirred solution of cupric acetate monohydrate, prepared by adding 0.79 g (0.004 mol) of cupric acetate monohydrate to 25 ml of water. After the addition was complete, stirring was continued for one-half hour before the light blue precipitate was collected by filtration and washed with 500 ml of water before air drying. The yield was 0185 g, 34%. On heating a sample of this material to 209° C. it decomposed.

Analysis Calcd. for $C_{42}H_{78}O_{25}P_2Cu_3$: C, 40.82; H, 6.36. Found: C, 40.59; H, 6.18.

EXAMPLE 33

(Hydrocortisone-21-phosphato)$_{2n}$-(aqua)$_{7n}$-copper(II)$_{3n}$, [Cu(II)$_{3n}$(HC-21-phosphate)$_{2n}$(H$_2$O)$_{7n}$].

This coordination compound was prepared by dissolving 1 g (0.002 mol) of the disodium salt of hydrocortisone-21-phosphate in 100 ml of water, adding 1 drop of concentrated hydrochloric acid to give a pH of 6.6 and adding this solution dropwise to a stirred solution of cupric chloride dihydrate (1 g, 0.006 mol) in 50 ml of water. After the addition was complete the mixture was allowed to stir for one hour and the light blue precipitate collected by filtration, washed with 200 ml of water, air dried and weighed (400 mg, 33% yield). A sample of this material gradually decomposed on heating to 210° C.

Analysis Calcd. for $C_{42}H_{74}O_{23}P_2Cu_3$: C, 42.05; H, 6.22. Found: C, 42.00; H, 6.21.

EXAMPLE 34

(Hydrocortisone-21-hemisuccinato)$_{4n}$-(aqua)$_{6n}$-copper(II)$_{2n}$, [Cu(II)$_{2n}$(HC-21-hemisuccinate)$_{4n}$(H$_2$O)$_{6n}$].

This coordination compound was prepared by dissolving 1 g (0.002 mol) of hydrocortisone-21-hemisuccinic acid in 250 ml of water with concentrated ammonium hdyroxide. The resulting pH was 9.0 and was adjusted to pH 7.0 with a 10% solution of hydrochloric acid. This solution was then added dropwise to a stirred solution of cupric chloride dihydrate (1 g, 0.006 mol) dissolved in 250 ml of water. The resulting light blue-green precipitate was collected, air dried and weighed (1 g, 96% yield). A sample of this material decomposed on heating over the range of 191° to 195° C.

Analysis Calcd. for $C_{100}H_{144}O_{38}Cu_2$: C, 57.71; H, 6.97. Found: C, 57.41; H, 7.26.

EXAMPLE 35

(Hydrocortisone-21-hemisuccinato)$_{4n}$-(aqua)$_{7n}$-copper(II)$_{2.5n}$[Cu(II)$_{2.5n}$(HC-21-hemisuccinate) $_{2n}$(H$_2$O$_{7n}$)].

This coordination compound was prepared by dissolving 1 g (0.002 mol) of hydrocortisone-21-hemisuccinic acid in 20 ml of water with concentrated ammonium hydroxide. The resulting pH was 9.5. This solution was then added dropwise to a stirred solution of cupric chloride dihydrate (1 g, 0.006 mol) dissolved in 15 ml of water. The light blue precipitate which formed was collected by filtration, air dried and weighed (1.2 g, 99% yield). A sample of this material decomposed on heating over the range of 196° to 197° C.

Analysis Calcd. for $C_{100}H_{160}O_{46}Cu_5$: C, 49.71; H, 6.68. Found: C, 49.91; H, 6.63.

EXAMPLE 36

(9α-Fluoro-11$_\beta$, 17$_{60}$, 21-trihydroxy-16$_{60}$-methyl-1,4-pregnadiene-3,20-dione-21 -phosphato)$_{2n}$-(aqua)$_{7n}$-copper(II)$_{3n}$, [Cu(II)$_{3n}$(dexamethasone-21-phosphate)$_{2n}$(H$_2$O)$_{7n}$].

This coordination compound was prepared by dropping a solution of the disodium salt of dexamethasone-21-phosphate (9 g, 0. mol) dissolved in 100 ml of water, into a stirred solution of 100 ml of water containing 4.6 g (0.003 mol) of cupric chloride dihydrate. After the addition was completed an additional 300 ml of water was added. The resulting light blue precipitate was collected by filtration, washed with water, air dried and weighed (8.1 g, 75% yield). A sample of this material gradually decomposed on heating to 300° C.

Analysis Calcd. for $C_{88}H_{140}O_{46}P_4F_4Cu_6$: C, 42.02; H, 5.61. Found: C, 42.04; H, 5.5.

EXAMPLE 37

(9α-Fluoro-11$_\beta$, 17α-21-trihydroxy-16α-methyl-1,4-pregnadiene-3,20-dione -21-phosphato)$_{2n}$-(aqua)$_{1.5n}$-copper(II)$_{3n}$, [Cu(II)$_{3n}$(dexamethasone-21-phosphate)$_{2n}$(H$_2$O)$_{1.5n}$)9 .

This coordination compound was prepared by taking 2 g (0.0008 mol) of the material prepared in example 36 and suspending it in a stirred methanol for two hours to remove some of the water of hydration. After air drying this material was dried at 45° C. and 15 mm Hg overnight. A sample of this material also decomposed on heating to 300° C.

Analysis Calcd. for $C_{88}H_{118}O_{35}P_4F_4Cu_6$° C., 45.62; H, 5.13. Found: C, 45.51; H, 5.48.

EXAMPLE 38

[1-(p-Chlorobenzoyl)-5-methoxy-2-methylindole-3-acetato]$_{4n}$-(aqua)$_{4n}$-copper(II)$_{2n}$, Cu(II)$_{2n}$[1-(p-chlorobenzoyl)-5-methoxy-2-methylindole-3-acetate]$_{4n}$(H$_2$O)$_{4n}$.

This coordination compound was synthesized from the sodium salt of the parent acid (5 g, 0.014 mol), prepared as in example 1 except 1-(p-chlorobenzoyl)-5-methoxy-2-methylindole-3-acetic acid was used in place of L-tryptophan, in 200 ml of water. The solution of the sodium salt was dropped into a stirred 300 ml water solution of cupric chloride dihydrate (1.95 g, 0.013 mol). The resultant green precipitate was collected by filtration, washed with water, air dried and weighed (5.6 g, 98% yield). A sample of this material decomposed on heating to 190° C.

Analysis Calcd. for $C_{76}H_{68}O_{20}N_4Cl_4Cu_2$: C, 56.13; H, 4.21; N, 3.44. Found: C, 56.00; H, 3.78; N, 3.40.

EXAMPLE 39

[1-(p-Chlorobenzoyl)-5-methoxy-2-methylindole-3-acetato]$_{4n}$-(acetone)$_{2n}$-copper(II)$_{2n}$, Cu(II)$_{2n}$[1-p-chlorobenzoyl)-5-methoxy-2-methylindole-3-acetate] $_{4n}$(CH$_3$COCH$_3$)$_{2n}$.

This coordination was prepared in a manner similar to that described for example 38, using twice the amount of parent acid and cupric chloride dihydrate. However, after the green precipitate was collected by filtration it was leached with 1 liter of acetone and the leachate concentrated to 500 ml. On standing, additional green crystals formed in the acetone solution. These were collected by filtration, air dried and weighed (6.9 g, 62% yield). A sample of this material decomposed on heating up to and over the range of 190° to 193° C.

Analysis Calcd. for $C_{82}H_{72}O_{18}N_4Cl_4Cu_2$: C, 58.81; H, 4.79; N, 3.21. Found: C, 58.96; H, 4.34; N, 3.35.

EXAMPLE 40

(4-n-Butyl-1,2-diphenyl-3,5-pyrazolidinedione)$_{2n}$-copper(II)$_n$, [Cu(II)$_n$(4-n-butyl-1,2-diphenyl-3,5-pyrazolidinedione)$_{2n}$].

A solution of the sodium salt of the parent compound 4-n-butyl-1,2-diphenyl-3,5-pyrazolidinedione, (5 g, 0.015 mol) dissolved in 50 mol of 95% ethanol was diluted with 150 mol of H$_2$O. To this stirred solution was added 2.73 g (0.007 mol) of cupric acetate monohydrate, in small aliquats. The greenish precipitate which formed was collected by filtration, dried at 95° C. and 15 mm Hg overnight and weighed (4.5 g, 94.5% yield). A sample of this material softened and melted over the range of 65° to 75° C.

Analysis Calcd. for $C_{28}H_{38}N_4O_4Cu$; C, 67.29; H, 5.65; N, 8.26. Found: C, 67.61; H, 5.43; N, 8.28.

EXAMPLE 41

(17-Hydroxy-3-oxo-17α-pregn-4,6-diene-21-carboxalato)$_{2n}$-(aqua)$_{2n}$-copper(II)$_n$, [Cu(II)$_n$(17-hydroxy-3-oxo-17α-pregn-4,6-diene-21-carboxylato)$_{2n}$(H$_2$O)$_{2n}$.

The potassium salt of the parent acid (17-hydroxy-3-oxo-17α-pregn-4,6-diene-21-carboxylic acid) (5 g, 0.013 mol) was dissolved in 50 ml of water. This solution was dropped into a stirred solution of cupric acetate monohydrate, prepared by dissolving 5 g (0.012 mol) in 50 ml of water. After the addition was completed the mixture was left to stir for an additional one-half hour before removing the precipitate by filtration. This precipitate was washed with 500 ml of water before air drying followed by drying at 30° and 15 mm Hg over the weekend. A 5 g, 24% yield was obtained. A sample of this material decomposed on heating over the range of 168°–169° C. This material was redried at 40° and 15 mm Hg before obtaining elemental analysis.

Analysis Calcd. for $C_{88}H_{128}O_{22}Cu_2$: C, 64.88; H, 7.67. Found: C, 64.44; H, 7.87.

EXAMPLE 42

Bisdiethyldithiocarbamatocopper(II) [Cu(II)(DDC)$_2$].

Three gms (0.013 mol) of sodium diethyldithiocarbamate was stirred in approximately 300 ml of deionized distilled water and the solution filter to remove an insoluble particulate material. An aqueous solution of anhydrous CU(II)Cl$_2$ was prepared by dissolving 1.13 gms (0.008 mol) in approximately 25 ml of deionized distilled water and filtering. The filtrate was dropped into the virogously stirred solution of sodium diethyldithiocarbamate. The resulting brown precipitate was filtered with a scintered glass filter funnel, washed three times with deionized distilled water, and air dried while attached to a laboratory vacuum line (approximately 15 mm Hg). A sample of the air dried precipitate (1.9 gm) melted with decomposition over the 194° to 916° C. range.

Analysis calculated for $C_{10}H_{20}N_2S_4Cu(H_2O)_{0.75}$: C, 32.13; H, 5.76; N, 7.50. Found: C, 31.79; H, 5.40; N, 7.51.

Several of the above described compounds were prepared and tested in accordance with the following recognized test methods:

1. Acetic acid-induced writhing test as described in Koster et al., "Acetic Acid for Analgesic Screening", Fed. Proc. 18, 412 (1959), incorporated by reference herein; and 2. Adjuvant-induced arthritic pain as described in:

S. KUZNA, et al., Measurement of Arthritic Pain and Effects of Analgesics in the Adjuvant-Treated Rat, Chem. Pharm. Bull. 23, 1184–1191 (1975);

C. A. WINTER, et al., Analgesic Activity of Diflunisal in Rats with Hyperalygesia Induced by Freud's Adjuvant, J. Pharmacol. Exp. Ther. 211, 678–685 (1979; and M. E. ROSENTHALE, et al., Adjuvant Arthritis:Immuno-Pathological and Hyperalgesic Features, Fed. Proced. 41, 2577–2582 (1982), incorporated by reference herein.

More particularly, the following tests were performed with the following results.

Acetic acid-induced writhing test

Groups of 10 ICR male mice (Taisho Pharmaceutical Co. Research Center) were used to study each dose of every compound. Ligands or complexes were administered orally or subcutaneously in 0.1 ml of vehicle per 10 g of body weight 30 minutes before the intrapertioneal injection of 0.1 ml of 0.7% acetic acid solution per 10 g of body weight. Number of writhes were counted for each mouse during a period of 10 to 20 min after acetic acid injection. Inhibitory percent was calculated by comparison with the number of writhes in the non-treated control, vehicle-treated, and acetic acid-injected group. The ED$_{50}$ value and 95% confidence limits were calculated from the inhibitory percent by the method of Litchfield and Wilcoxon.

Adjuvant-induced arthritic pain

Groups of 5–6 male Sprague-Dawley rats (Taisho Pharmaceutical Co. Research Center) weighing 140 to 160 g at the time of Mycobacterium butyricum (adjuvant, Difco Laboratories, Detroit, Mich.) injection were used to study each compound. Rats were injected intradermally at the base of the tail with 0.1 ml of a parafin oil suspension of 0.5 mg of heat-killed mycobacterium. Fifteen to 19 days later, drugs were administered orally or subcutaneously in 0.5 ml of vehicle per 100 g of body weight to rats showing the nociceptive reaction, vocalization following a gentle flexion of the tarsal-tibial joint of the inflamed hind-paw. Vocalization responses were measured every hour for 5 hours. Rats that did not show the vocalization response were regarded as positive for anti-nociceptive activity. The ED$_{50}$ value and 95% confidence limits were calculated from the positive rate for non-treated controls, vehicle-treated adjuvant arthritic rats, by the method of Litchfield and Wilcoxin.

Drug formulations

All drugs were suspended with 5% gum arabic in saline solution or wetted with enough propylene glycol to give a final concentration of 4% propylene glycol and the wetted solid suspended in 1.4% polyvinyl alcohol in saline.

Results

Of the three mononuclear complexes, Cu(II)(anthranilate)$_2$ and Cu(II) (salicylate)$_2$ were more effective than their parent ligands while Cu(II)-(3,5-dips)$_2$ was slightly less effective than its parent ligand as analgesics in the acetic acid-induced writhing model of pain following oral administration as a 5% gum arabic suspension in saline (Table I). When these complexes were administered in a mixture of 5% propylene glycol and 1.4% polyvinyl alcohol in saline (PG-PVA vehicle), Cu(II)(anthranilate)$_2$ and Cu(II)(salicylate)$_2$ were again more effective than their parent ligands and Cu(II)(3,5-dips)$_2$ was only as effective as its parent ligand following oral administration in this pain model. All three copper complexes were more effective than their parent ligands following subcutaneous (s.c.) administration and this route of administration was more efficacious than oral administration. This increase in potency ranged from 2-to 10-fold, and all three of these square planar complexes were essentially equipotent ED$_{50}$=0.2 mmol/kg.

All three binuclear complexes; Cu(II)$_2$(aspirinate)$_4$, Cu(II)$_2$(niflumate)$_4$, and Cu(II)$_2$(indomethacin)$_4$ were more effective than their parent ligands in the acetic acid-induced writhing pain model following oral administration in both 5% gum arabic and PG-PVA, and they were most effective following administration in PG-PVA (Table II). All three of these complexes were also more effective than their parent ligands following s.c. administration, with ED$_{50}$ values ranging from 0.02 to 0.003 mmol/kg. These data show that these binuclear complexes were 10-to 50-fold more effective than the mononuclear complexes, consistent with potentially greater complex stability due to steric interference to approach to the open bonding site on copper by competing ligands and greater lipophilicity.

Data obtained for the analgesic activity of Cu(II)(chloride)$_2$ and Cu(II)$_2$(acetate)$_4$ (Table II), mononuclear and binuclear complexes respectively, in the writing model show that these compounds were not as effective as the more strongly bonded complexes (Tables I and II), with ED$_{50}$ values of only 0.60 and 0.32 mmol/kg respectively. However, Cu(II)$_2$(acetate)$_4$ was more effective than anthranilic acid, salicylic acid, and aspirin and Cu(II)(chloride)$_2$ was more effective than salicylic acid and essentially as effective as anthranilic acid.

Data in Table III compare analgesic activities Cu(II)(anthranilate)$_2$, Cu(II)(salicylate)$_2$, and Cu(II)(3,5-dips)$_2$ with their parent ligand in the adjuvant-induced pain model. Cu(II)(anthranilate)$_2$ was less effective than its parent ligand following oral administration in 5% gum arabic and, apparently, following oral administration in the PG-PVA vehicle. Cu(II)(salicylate)$_2$ was more effective than its parent ligand following oral administration in both vehicles, while Cu(II)(3,5-dips)$_2$ was essentially equipotent with its ligand following oral administration in 5% gum arabic and, apparently, more effective than its parent ligand following oral administration in PG-PVA. Each of these three copper complexes was 2- to 4-times as effective as its parent ligand following s.c. administration.

As shown in Table IV, Cu(II)$_2$(aspirinate)$_4$ and Cu(II)$_2$(niflumate)$_4$ were more effective than their parent ligand in the adjuvant-induced pain model following oral administration in 5% gum arabic while all three binuclear complexes were more effective than their parent ligand following oral administration in the PG-PVA vehicle. In addition, all three complexes were either as effective or more effective following s.c. administration than they were following oral administration. With $ED_{50}$ values ranging from 0.06 to 0.002 mmol/kg in this pain model, these complexes appear to be as effective or slightly more effective in this pain model than in the writhing pain model. Both Cu(I-I)(chloride)$_2$ and Cu(II)$_2$(acetate)$_4$ were devoid of analgesic activity in this pain model at does which produced statistically significant analgesic effects in the writhing pain model.

Another matter of interest is the comparison of the analgesic activity of these copper complexes with the activity of morphine. $ED_{50}$ values for morphine in the writhing and adjuvant arthritis pain models were found to be 0.002 mmol/kg (Table V), the same value obtained for Cu(II)$_2$(indomethacin)$_4$ following oral and s.c. administration in both the writhing pain model (Table II) and the adjuvant arthritis pain model (Table IV).

To evaluate the time course of analgesia associated with a non-steroidal anti-inflammatory agent and its copper complex, salicylic acid and its complex were compared in the adjuvant-arthritis pain model following oral administration in 5% gum arabic. Data presented in FIG. 1 show that analgesic activity increased in a dose-related manner and the (CU(II)(salicylate)$_2$ was 7-to 10-times as effective as salicylic acid. In addition, the analgesic activity of Cu(II)(salicylate)$_2$ appears to be more sustained than the analgesic activity of salicylic acid since analgesia associated with salicylic acid treatment began to decline in the 3 to 4 hr interval following treatment while (Cu(II)(salicylate)$_2$ analgesia was maintained or increased throughout the entire 5 hour post-treatment interval. This sustained analgesic effect may be the result of slower and prolonged gastric absorption of Cu(II)(salicylate)$_2$ in comparison with salicylic acid due to its greater lipophilicity and reduced solubility in the aqueous vehicle.

As shown in Table VI, copper complexes of amino acids were effective while their ligands were ineffective in the acetic acid-induced pain model but ineffective in the adjuvant-induced arthritic pain model. Even though Cu(II)(L-alaninate)$_2$, Cu(II)(L-cystinate), and Cu(II)(glycinate)$_2$ were less active than the other copper complexes, including Cu(II)(chloride)$_2$ and Cu(II)$_2$(acetate$_4$, the fact that each of these complexes was more active than its parent ligand suggests that this class of copper complexes may also be important physiologic modulators of nociception.

Table VII shows prolonged duration of analgesic effect for both Cu(II)(DDC)$_2$ and Cu(II)$_2$(Indomethacin)$_4$ complexes.

Table VIII shows the reduction in Cu(II)(DDC)$_2$ and Cu(II)$_2$(Indomethacin)$_4$ induced analgesia by Naloxone, an opioid antagonist. Naloxone antagonism of analgesia shows that the copper complexes have opioid-like analgesic activity.

Table IX shows potentiation of opioid analgesia by Cu(II)$_2$(Indomethacin)$_4$.

Discussion

It was generally found that analgesic activities of copper complexes were greater following oral treatment using the PG-PVA suspending system than they were with the gum arabic suspending system. A copper complex firmly bonded to gum arabic, or competition by gum arabic for bonding sites on copper and ligand exchange, may account for reduced activity associated with gum arabic suspension. Neither propylene glycol nor polyvinyl alcohol has functional groups capable of causing this interference.

Subcutaneous administration in PG-PVA nearly always produced greater analgesic effects than oral administration. This is accounted for as being due to more complete absorption following s.c. administration as compared to uncertain absorption following oral administration. Since hydrophilicity favors solution in aqueous vehicles and gastric absorption, parent ligands being more hydrophilic than these copper complexes are likely to be absorbed more rapidly even though greater lipid membrane transport is facilitated by lipophilic character. In spite of these relative differences in absorbability which would facilitate parent ligand activity, these copper complexes were still more effective than their parent ligands.

Dissociation of these copper complexes in the stomach can not be used to account for analgesic activities of these complexes since their ligands and more freely dissociable forms of copper, Cu(II)(chloride)$_2$ and Cu(II)$_2$(acetate)$_4$, have less activity than observed for these complexes. In addition, copper complexes have antisecretory activity and decrease gastric acidity.

It is phenomenal that the copper complex of acetic acid is effective in preventing pain in the writhing model since the injection of acetic acid, its ligand, is used to produce pain in this model. In addition, irritant-induced anti-inflammatory and concomitant stress-induced analgesic activity can not be used to explain these results since the most likely irritant, Cu(II)(chloride)$_2$, was the least effective compound.

These data are consistent with the notion that non-steroidal anti-inflammatory agents form copper complexes in vivo and support the possibility that copper complex formation in vivo accounts for the analgesic activity of these anti-inflammatory agents as well. The observation that copper complexes are absorbed and mediate analgesia following tissue distribution suggests physiologic and biochemical roles for copper in analgesia.

TABLE I

Analgesic effects of parent ligands and copper complexes on acetic acid induced writhing in mice

| Compound | Oral (mmol/kg)$^a$ | Oral (mmol/kg)$^b$ | Subcutaneous (mmol/kg)$^b$ | % Inhibition | ED50 (mmol/kg) (95% C.L.) |
|---|---|---|---|---|---|
| Anthranilic acid | 1.46 | | | 18 | >1.46 |
| | | 2.19 | | 45** | >2.19 |
| | | | 0.27 | 30 | 0.64 |
| | | | 0.55 | 36 | (0.33–1. |
| | | | 1.09 | 71** | |
| Cu(II)(anthranilate)$_2$ | 0.15 | | | 25 | 0.50 |
| | 0.30 | | | 47*** | (0.18–1.38) |
| | 0.60 | | | 50** | |

TABLE I-continued

Analgesic effects of parent ligands and copper complexes on acetic acid induced writhing in mice

| Compound | Oral (mmol/kg)[a] | Oral (mmol/kg)[b] | Subcutaneous (mmol/kg)[b] | % Inhibition | ED50 (mmol/kg) (95% C.L.) |
|---|---|---|---|---|---|
|  |  | 0.89 |  | 50** | >0.89 |
|  |  |  | 0.07 | 30 | 0.22 |
|  |  |  | 0.15 | 42* | (0.08–0.58) |
|  |  |  | 0.30 | 57** |  |
| Salicylic acid | 0.91 |  |  | 29 | 2.13 |
|  | 1.81 |  |  | 33* | (1.19–3.83) |
|  | 3.62 |  |  | 73** |  |
|  |  | 2.17 |  | 38* | >2.17 |
|  |  |  | 0.54 | 25 | 1.02 |
|  |  |  | 1.09 | 52** | (0.65–1.62) |
|  |  |  | 2.17 | 80*** |  |
| Cu(II)(salicylate)$_2$ | 0.30 |  |  | 30 | 0.65 |
|  | 0.59 |  |  | 43* | (0.33–1.27) |
|  | 1.18 |  |  | 69*** |  |
|  |  | 0.30 |  | 20 | 1.53 |
|  |  | 0.59 |  | 27 | (0.61–3.80) |
|  |  | 1.18 |  | 46* |  |
|  |  |  | 0.07 | 40 | 0.17 |
|  |  |  | 0.15 | 48* | (0.05–0.39) |
|  |  |  | 0.30 | 66*** |  |
| 3,5-Dips | 0.22 |  |  | 44* | 0.27 |
|  | 0.45 |  |  | 66** | (0.14–0.52) |
|  | 0.90 |  |  | 88*** |  |
|  |  | 0.22 |  | 19 | 0.44 |
|  |  | 0.45 |  | 56** | (0.29–0.67) |
|  |  | 0.90 |  | 78*** |  |
|  |  |  | 0.11 | 22 | 0.23 |
|  |  |  | 0.23 | 49* | (0.13–0.30) |
|  |  |  | 0.45 | 91*** |  |
| Cu(II)(3,5-dips)$_2$ | 0.20 |  |  | 35 | 0.40 |
|  | 0.40 |  |  | 48* | (0.17–0.98) |
|  | 0.80 |  |  | 66** |  |
|  |  | 0.20 |  | 26 | 0.43 |
|  |  | 0.40 |  | 56* | (0.20–0.91) |
|  |  | 0.79 |  | 62*** |  |
|  |  |  | 0.10 | 27 | 0.20 |
|  |  |  | 0.20 | 45** | (0.12–0.35) |
|  |  |  | 0.40 | 74*** |  |

[a] administered in 5% gum arabic in saline,
[b] administered in 5% propylene glycol and 1.4% polyvinyl alcohol in saline for s.c. administration.
*$p < 0.05$,
**$p < 0.01$,
***$p < 0.001$ versus vehicle treated group.

TABLE II

Analgesic effects of parent ligands and copper complexes on acetic acid induced writhing in mice

| Compound | Oral (mmol/kg)[a] | Oral (mmol/kg)[b] | Subcutaneous (mmol/kg)[b] | % Inhibition | ED50 (mmol/kg) (95% C.L.) |
|---|---|---|---|---|---|
| Aspirin | 0.56 |  |  | 29 | 1.30 |
|  | 1.11 |  |  | 42* | (0.57–2.95) |
|  | 2.22 |  |  | 66** |  |
|  |  | 0.21 |  | 32 | 0.48 |
|  |  | 0.42 |  | 41* | (0.22–1.04) |
|  |  | 0.84 |  | 67*** |  |
|  |  |  | 0.28 | 28 | 0.52 |
|  |  |  | 0.56 | 57** | (0.28–1.96) |
|  |  |  | 1.11 | 71*** |  |
| Cu(II)$_2$(aspirinate)$_4$ | 0.06 |  |  | 37 | >0.24 |
|  | 0.12 |  |  | 38* |  |
|  | 0.24 |  |  | 33 |  |
|  |  | 0.09 |  | 32* | 0.14 |
|  |  | 0.18 |  | 59** | (0.09–0.25) |
|  |  | 0.36 |  | 80*** |  |
|  |  |  | 0.03 | 36 | 0.04 |
|  |  |  | 0.06 | 59* | (0.03–0.08) |

TABLE II-continued

Analgesic effects of parent ligands and copper complexes on acetic acid induced writhing in mice

| Compound | Oral (mmol/kg)[a] | Oral (mmol/kg)[b] | Subcutaneous (mmol/kg)[b] | % Inhibition | ED50 (mmol/kg) (95% C.L.) |
|---|---|---|---|---|---|
| Niflumic acid | | | 0.24 | 82*** | |
| | 0.18 | | | 52** | 0.15 |
| | 0.35 | | | 65*** | (0.05–0.49) |
| | 0.71 | | | 75*** | |
| | | 0.13 | | 38* | 0.21 |
| | | 0.27 | | 51** | (0.11–0.40) |
| | | 0.53 | | 80*** | |
| | | | 0.04 | 21 | 0.10 |
| | | | 0.09 | 54** | (0.05–0.19) |
| | | | 0.18 | 64** | |
| Cu(II)$_2$(niflumate)$_4$ | 0.04 | | | 37** | 0.09 |
| | 0.08 | | | 48*** | (0.03–0.31) |
| | 0.16 | | | 60*** | |
| | | 0.06 | | 33* | 0.10 |
| | | 0.12 | | 57*** | (0.05–0.20) |
| | | 0.24 | | 73*** | |
| | | | 0.01 | 37* | 0.02 |
| | | | 0.02 | 48** | (0.01–0.08) |
| | | | 0.04 | 58*** | |
| Indomethacin | 0.01 | | | 36* | 0.04 |
| | 0.03 | | | 42** | (0.01–0.13) |
| | 0.06 | | | 58** | |
| | | 0.007 | | 27 | 0.01 |
| | | 0.014 | | 60** | (0.01–0.03) |
| | | 0.028 | | 68*** | |
| | | | 0.007 | 19 | 0.02 |
| | | | 0.014 | 36 | (0.01–0.04) |
| | | | 0.056 | 60** | |
| Cu(II)$_2$(indomethacin)$_4$ | 0.006 | | | 33 | 0.012 |
| | 0.013 | | | 50** | (0.005–0.028) |
| | 0.025 | | | 73*** | |
| | | 0.001 | | 38 | 0.002 |
| | | 0.002 | | 53** | (0.001–0.003) |
| | | 0.004 | | 75*** | |
| | | | 0.002 | 34 | 0.003 |
| | | | 0.003 | 53* | (0.001–0.006) |
| | | | 0.006 | 70** | |
| Cu(II)$_2$(chloride)$_2$ | | | 0.56 | 48** | 0.60 |
| | | | 1.12 | 69*** | (0.30–1.2) |
| | | | 2.24 | 83*** | |
| Cu(II)$_2$(acetate)$_4$ | | | 0.21 | 42* | 0.32 |
| | | | 0.41 | 59*** | (0.08–30) |
| | | | 0.83 | 61*** | |

[a]administered in 5% gum arabic in saline,
[b]administered in 5% propylene glycol and 1.4% polyvinyl alcohol in saline for s.c. administration.
*p < 0.05,
**p < 0.01,
***p < 0.001 versus vehicle treated group.

TABLE III

Analgesic effects of parent ligands and their copper complexes on adjuvant-induced arthritic pain in rats.

| Compound | Oral (mmol/kg)[a] | Oral (mmol/kg)[b] | Subcutaneous (mmol/kg)[b] | % Inhibition | ED50 (mmol/kg) (95% C.L.) |
|---|---|---|---|---|---|
| Anthranilic acid | 0.36 | | | 23 | 0.83 |
| | 0.73 | | | 41 | (0.43–1.61) |
| | 1.46 | | | 73 | |
| | | 1.46 | | 37 | >1.44 |
| Cu(II)(anthranilate)$_2$ | 0.30 | | | 0 | >0.60 |
| | 0.60 | | | 10 | |
| | | 0.60 | | 17 | >0.60 |
| | | | 0.07 | 20 | 0.19 |
| | | | 0.15 | 43 | (0.009–0.42) |
| | | | 0.30 | 63 | |
| Salicylic acid | 1.09 | | | 27 | 2.33 |
| | 2.17 | | | 57 | (1.13–4.79) |

TABLE III-continued

Analgesic effects of parent ligands and their copper complexes on adjuvant-induced arthritic pain in rats.

| Compound | Oral (mmol/kg)[a] | Oral (mmol/kg)[b] | Subcutaneous (mmol/kg)[b] | % Inhibition | ED50 (mmol/kg) (95% C.L.) |
|---|---|---|---|---|---|
| | 4.34 | | | 37 | |
| | | 0.72 | | 33 | 1.83 |
| | | 1.44 | | 43 | (0.49–6.81) |
| | | 2.88 | | 60 | |
| Cu(II)(salicylate)$_2$ | 0.15 | | | 27 | 0.25 |
| | 0.30 | | | 57 | (0.13–0.43) |
| | 0.59 | | | 73 | |
| | | 0.15 | | 30 | 0.12 |
| | | 0.30 | | 47 | (0.13–0.48) |
| | | 0.59 | | 90 | |
| | | | 0.04 | 20 | 0.12 |
| | | | 0.07 | 37 | (0.05–0.29) |
| | | | 0.15 | 57 | |
| 3,5-Dips | 0.22 | | | 30 | 0.36 |
| | 0.45 | | | 53 | (0.20–0.66) |
| | 0.90 | | | 92 | |
| | | 0.45 | | 27 | >0.90 |
| | | 0.90 | | 43 | |
| Cu(II)(3,5-dips)$_2$ | 0.10 | | | 7 | 0.43 |
| | 0.20 | | | 20 | (0.20–0.93) |
| | 0.40 | | | 47 | |
| | | 0.40 | | 40 | >0.40 |
| | | | 0.05 | 23 | 0.12 |
| | | | 0.10 | 37 | (0.06–0.25) |
| | | | 0.20 | 70 | |

[a]administered in 5% gum arabic in saline,
[b]administered in 5% propylene glycol and 1.4% polyvinyl alcohol in saline for s.c. administration.

TABLE IV

Analgesic effects of parent ligands and their copper complexes on adjuvant-induced arthritic pain in rats.

| Compound | Oral (mmol/kg)[a] | Oral (mmol/kg)[b] | Subcutaneous (mmol/kg)[b] | % Inhibition | ED50 (mmol/kg) (95% C.L.) |
|---|---|---|---|---|---|
| Aspirin | 0.28 | | | 27 | 0.62 |
| | 0.56 | | | 43 | (0.32–1.36) |
| | 1.11 | | | 70 | |
| | | 0.56 | | 30 | 1.41 |
| | | 1.11 | | 40 | (0.50–3.96) |
| | | 2.22 | | 63 | |
| Cu(II)$_2$(aspirinate)$_4$ | 0.06 | | | 7 | 0.29 |
| | 0.12 | | | 17 | (0.13–0.65) |
| | 0.24 | | | 43 | |
| | | 0.03 | | 13 | 0.09 |
| | | 0.06 | | 30 | (0.04–0.21) |
| | | 0.12 | | 60 | |
| | | | 0.03 | 23 | 0.06 |
| | | | 0.06 | 50 | (0.03–0.12) |
| | | | 0.12 | 73 | |
| Niflumic acid | 0.18 | | | 13 | 0.42 |
| | 0.35 | | | 27 | (0.26–0.68) |
| | 0.71 | | | 87 | |
| | | 0.18 | | 23 | 0.48 |
| | | 0.35 | | 43 | (0.19–1.20) |
| | | 0.71 | | 60 | |
| Cu(II)$_2$(niflumate)$_4$ | 0.04 | | | 7 | 0.18 |
| | 0.08 | | | 13 | (0.09–0.38) |
| | 0.16 | | | 47 | |
| | | 0.16 | | 37 | >0.16 |
| | | | 0.01 | 17 | |
| | | | 0.02 | 50 | 0.03 |
| | | | 0.04 | 60 | (0.01–0.06) |
| Indomethacin | 0.001 | | | 27 | 0.003 |
| | 0.003 | | | 43 | (0.001–0.006) |
| | 0.006 | | | 77 | |
| | | 0.007 | | 23 | 0.02 |
| | | 0.014 | | 43 | (0.01–0.03) |

TABLE IV-continued

Analgesic effects of parent ligands and their copper complexes on adjuvant-induced arthritic pain in rats.

| Compound | Oral (mmol/kg)[a] | Oral (mmol/kg)[b] | Subcutaneous (mmol/kg)[b] | % Inhibition | ED50 (mmol/kg) (95% C.L.) |
|---|---|---|---|---|---|
| Cu(II)$_2$(indomethacin)$_4$ | | 0.028 | | 70 | |
| | 0.003 | | | 27 | 0.007 |
| | 0.006 | | | 47 | (0.004–0.15) |
| | 0.013 | | | 70 | |
| | | 0.001 | | 20 | 0.002 |
| | | 0.002 | | 40 | (0.001–0.003) |
| | | 0.003 | | 87 | |
| | | | 0.001 | 17 | 0.002 |
| | | | 0.002 | 43 | (0.001–0.005) |
| | | | 0.003 | 60 | |
| Cu(II)(chloride)$_2$ | | 2.24 | | 0 | >2.24 |
| | | | 2.24 | 3 | >2.24 |
| Cu(II)$_2$(acetate)$_4$ | | 0.83 | | 0 | >0.83 |
| | | | 0.83 | 3 | >0.83 |

[a]administered in 5% gum arabic in saline,
[b]administered in 5% propylene glycol and 1.4% polyvinyl alcohol in saline for s.c. administration.

TABLE V

Analgesic activity of morphine in the acetic acid induced writhing (W) and adjuvant arthritis (AA) pain models.

| Dose (mmol/kg)[a] | % Inhibition | ED50 (mmol/kg) (95% of C.L.) W | ED50 (mmol/kg) (95% of C.L.) AA |
|---|---|---|---|
| 0.001 | 35 | 0.002 | |
| 0.002 | 44* | (0.001–0.003) | |
| 0.004 | 89*** | | |
| 0.001 | 20 | | |
| 0.002 | 40 | | 0.002 |
| 0.004 | 60 | | (0.001–0.005) |

[a]Administered subcutaneously as the hydrochloride salt in saline.

TABLE VI

Analgesic effects of amino acids and their copper complexes on acetic acid induced writhing in mice and adjuvant-induced arthritic pain in rats.

| Compound | Oral (mmol/kg)[a] | % Inhibition | ED50 (mmol/kg) (95% C.L.) |
|---|---|---|---|
| L-alanine | 4.49 | 14 | >4.49 |
| Cu(II)(L-alaninate)$_2$ | 0.42 | 22 | 0.92 |
| | 0.83 | 48** | (0.54–1.56) |
| | 1.67 | 71** | |
| | 0.42[b] | 0 | >0.42 |
| L-cysteine | 3.30 | −5 | >3.30 |
| Cu(II)(L-cystinate) | 0.33 | 35* | >0.33 |
| | 0.33[b] | 0 | >0.33 |
| Glycine | 5.33 | 36* | >5.33 |
| Cu(II)(glycinate)$_2$ | 1.89 | 48** | >1.89 |

[a]administered in 5% gum arabic in saline,
[b]activity in adjuvant-induced arthritic pain.
*p < 0.05,
**p < 0.01,
***p < 0.01 versus. vehicle treated group.

TABLE VII

Measurement of time of peak activity for Sodium Diethyldithiocarbonate (DDC), Cu(II) (DDC)$_2$ and Cu(II)$_2$ (indomethacin)$_4$ in the acetic acid-induced writhing mouse pain model.

| Compound | Dose (umol/kg) | Route | N | Inhibition % Time after administration (min) 30 | 60 | 120 | 180 | 240 |
|---|---|---|---|---|---|---|---|---|
| NaDDC | 584 | s.c. | 10 | 48 | 53* | 20 | 18 | |
| Cu(II)(DDC)$_2$ | 555 | s.c. | 10 | 29 | 42* | 45* | 29 | |
| Cu(II)$_2$(indomethacin)$_4$ | 2 | p.o. | 10 | 54** | 49* | 43 | 68* | 33 |

*p 0.05,
**p 0.01 versus PG-PVA saline vehicle treated group (t-test)
N: number of animals.

TABLE VIII

Naloxone reversal of analgesia in the acetic acid-induced writhing mouse pain model.

| Compound | Dose (umol/kg) | Route | N | % Inhibition | $ED_{50}$ umol/kg (95% C.L.) |
|---|---|---|---|---|---|
| $Cu(II)_2(DDC)_2$ | 555 | s.c. | 10 | 45* | |
| Naloxone + Cu(II) (DDC)$_2$ | 555 | s.c. | 10 | 29 | |
| $Cu(II)_2$ (indomethacin)$_4$ | 0.5 | p.o. | 10 | 43** | 0.6 (0.3–1.4) |
| | 1 | p.o. | 10 | 62*** | |
| | 2 | p.o. | 10 | 76*** | |
| Naloxone + Cu(II)$_2$ (indomethacin)$_4$ | 0.5 | p.o. | 10 | 19 | 1.1 (0.6–1.8) |
| Cu(II)$_2$ (indomethacin)$_4$ | 1 | p.o. | 10 | 52*** | |
| Cu(II)$_2$ (indomethacin)$_4$ | 2 | p.o. | 10 | 69 | |

*p 0.05,
**p 0.01,
***p 0.001 versus PG-PVA saline vehicle treated group (t-test)
N: number of animals.
Naloxone-HCL (3 umol/kg. i.v., in saline, Endo Lab.) was administered 5 min. before acetic acid injection.

TABLE IX

Comparison of the analgesic activity of Cu(II)$_2$(indomethacin)$_4$ and morphine in the acetic acid-induced writhing mouse pain model.

| Compound | Dose$^a$ umol/kg | N | % Inhibition | $ED_{50}$ umol/kg (C.L.) |
|---|---|---|---|---|
| Cu(II)$_2$(indomethacin)$_2$ | 0.5 | 10 | 21 | |
| | 1.0 | 10 | 46* | 1.5 (0.7–3.1) |
| | 2.0 | 10 | 54** | |
| Morphine HCl | 1.0 | 10 | 35** | 1.6 (1.0–2.5) |
| | 2.0 | 10 | 44** | |
| | 4.0 | 10 | 89**** | |
| Morphine HCl + Cu(II)$_2$(indomethacin)$_4$ | 1.0 | 10 | 50** | |
| | 2.0 | 10 | 85**** | 1.0 |
| (0.5 umol/kg) | 4.0 | 10 | 98**** | (0.3–1.7) |

*p 0.05 versus PG-PVA saline vehicle treated group (t-test).
**p 0.05 versus saline vehicle treatment group (t-test).
***p 0.01 versus saline vehicle treatment group (t-test).
**** p 0.001 versus saline vehicle treatment group (t-test).
$^a$administered orally.
$^b$administered subcutaneously just before morphine administration.
N: number of animals.

Having thus described my invention, I claim:

1. A method of treating algesia in a patient not suffering from inflammation comprising administering to said patient a therapeutically effective amount of an organic coordination compound of copper, said compound comprising the reaction product of copper and an amino acid or alkaline earth salt thereof.

2. The method of claim 1 wherein the copper coordination compound is administered in an amount of 2 to 165 mg. per kilogram of body weight.

3. The method of claim 2 wherein said compound is the reaction product of a compound selected from the group consisting of cupric chloride and cupric acetate and an amino acid or alkaline earth salt thereof.

4. The method of claim 3 where said amino acid is tryptophan.

5. The method of claim 3 where said amino acid is lysine.

6. The method of claim 4 wherein said compound is administered orally or parenterally.

7. The method of claim 5 wherein said compound is administered orally or parenterally.

* * * * *